(12) United States Patent  
Siegenthaler

(10) Patent No.: US 8,303,501 B2
(45) Date of Patent: Nov. 6, 2012

(54) APPLANATION TONOMETER

(75) Inventor: Fritz Siegenthaler, Gümligen (CH)

(73) Assignee: Haag-Streit AG, Koniz (CH)

(*) Notice: Subject to any disclaimer, the term of this patent is extended or adjusted under 35 U.S.C. 154(b) by 799 days.

(21) Appl. No.: 12/267,440

(22) Filed: Nov. 7, 2008

(65) Prior Publication Data

US 2009/0131779 A1    May 21, 2009

(30) Foreign Application Priority Data

Nov. 8, 2007    (EP) .................................... 07405322

(51) Int. Cl.
*A61B 3/16* (2006.01)

(52) U.S. Cl. ........................................................ 600/405

(58) Field of Classification Search .......... 600/398–400, 600/405
See application file for complete search history.

(56) References Cited

U.S. PATENT DOCUMENTS

| 5,070,875 A | 12/1991 | Falck et al. |
| 2004/0210123 A1 | 10/2004 | Davidson |

FOREIGN PATENT DOCUMENTS

| CH | 692127 A5 | 2/2002 |
| CH | 692129 A5 | 2/2002 |
| DE | 199 39 348 B4 | 10/2000 |
| EP | 1 018 930 B1 | 7/2000 |
| FR | 2 683 990 A1 | 5/1993 |
| WO | WO-99/16343 A1 | 4/1999 |

*Primary Examiner* — Brian Szmal

(74) *Attorney, Agent, or Firm* — Birch, Stewart, Kolasch & Birch, LLP

(57) ABSTRACT

A device (2) for determining an intraocular pressure of an eye comprises a measurement arrangement with a measurement body (44), attached to a measurement arm (40), for applanation of the eye and a rotary knob (10) which is attached to a shaft (6). The measurement arm (40) is attached radially to a pivot axis (32) and the measurement arrangement comprises a mechanical coupling between the rotary knob (10) and the pivot axis (32), with a rotation of the rotary knob (10) being able to generate an applanation force required for applanation of the eye. The mechanical coupling comprises tension transmission means (12) attached to the pivot axis (32) via a first lever arm (34), and to the rotational axis (8) of the shaft (6) via a second lever arm (6).

21 Claims, 2 Drawing Sheets

APPLANATION TONOMETER

TECHNICAL FIELD

The invention relates to a device for determining the intraocular pressure of an eye having a measurement arrangement comprising a measurement body, attached to a measurement arm, for applanation of the eye and a rotary knob which is attached to a shaft and can rotate about a rotational axis of the shaft, with the measurement arm being attached radially to a pivot axis, the measurement arrangement comprising a mechanical coupling between the rotary knob and the pivot axis, and a rotation of the rotary knob around the rotational axis being able to generate an applanation force required for applanation of the eye. Furthermore, the invention relates to a corresponding method for determining an intraocular pressure.

PRIOR ART

In opthalmology, determining the intraocular pressure of an eye of a patient is a common examination. It is used in particular for (early) diagnosis and monitoring of glaucoma diseases. Various methods and corresponding equipment are known to determine the intraocular pressure. For example, there are invasive methods, in which appropriate pressure sensors are directly inserted into the eye. In the case of non-invasive methods, a further distinction can be made between contact measurement equipment, where the eye is touched during the measurement, and contactless measurement equipment, where the eye is not touched directly during the measurement.

In the case of contactless measurement equipment, the eye is applanate, that is to say flattened, due to an air flow having a defined strength. In the process, the speed and extent of the applanation are detected using particular optics and the eye pressure is deduced from this.

For example, determining the intraocular pressure using a Goldmann applanation tonometer is an example of a non-invasive method. This equipment measures the force required for applanation of a defined region of the eye to be examined (in this case a circular surface region with a diameter of 3.06 mm, for example), with a measurement body typically used for the applanation comprising a planar applanation surface and the applanation force to be applied being able to be set using a rotary knob. This equipment is then typically calibrated so that the intraocular pressure can then be read off directly from a scale on the rotary knob.

There are countless possibilities for an applanation tonometer to generate the applanation force and to then transfer this force to the measurement body and apply it to the eye.

For example, a Goldmann applanation tonometer is known from WO 99/16343 by Heyraud. A weight is displaced along the rotational axis of a rotary knob by means of the rotary knob, with this displacement being converted to movement of the measurement probe towards the eye by means of a mechanism and with the applanation pressure being set in this way.

US 2004/0210123 A1 by J. D. Mueller discloses an applanation tonometer, in which a force sensor is displaced by turning an adjustment knob, with a driver positioned on the force sensor pushing the lower end of a lever arm, mounted such that it can rotate, backwards (in the housing), so that the measurement head at the other end of the lever arm is pressed against the eye. The force sensor now measures the amount of force required for the applanation of a particular surface, generates a signal corresponding to the measured applanation force and sends it to a display, positioned on the tonometer or elsewhere, on which the measured applanation force or the intraocular pressure derived therefrom is displayed.

Although these types of equipment work flawlessly, they have the disadvantage of a complex design and are thus relatively expensive to produce. Usually, a complex and hence expensive balancing—and often, too, calibration—of the equipment is also required.

SUMMARY OF THE INVENTION

It is an object of the invention to develop a device, belonging to the technical field mentioned initially, for determining the intraocular pressure of an eye which, on the one hand, can be produced in a simple and therefore cost-effective manner, and, on the other hand, however still has a high quality and allows precise determination of the intraocular pressure. It is a further object of the invention to develop a corresponding method for determining the intraocular pressure of an eye.

The solution of the object is defined by the features of Claim 1. The device for determining the intraocular pressure of an eye of a patient comprises, inter alia, a measurement arrangement, which in turn comprises a measurement body, attached to a measurement arm, for the applanation of the eye and a rotary knob, attached to a shaft, which can rotate around a rotational axis of the shaft. The measurement arm is attached radially to a pivot axis and the measurement arrangement furthermore comprises a mechanical coupling between the rotary knob and the pivot axis. Rotation of the rotary knob around the rotational axis can generate the applanation force required for the applanation of the eye. According to the invention, the mechanical coupling now comprises tension transmission means, which, on the one hand, are attached to the pivot axis via a first lever arm and, on the other hand, are attached to the rotational axis of the shaft via a second lever arm.

Such equipment, where the intraocular pressure is caused by applanation of the surface of the eye, that is to say the cornea, is typically referred to as an applanation tonometer.

The sole purpose of the tension transmission means is the transmission of tension forces. That is to say, the force due to the rotation of the rotational axis, which acts on the end of the tension transmission means attached to the rotational axis, is transmitted by the tension transmission means to its other end and, from there, it exerts a torque on the pivot axis via the first lever arm, which pivot axis is accordingly set in rotation or pivoted. When the rotational axis is rotated by means of the rotary knob, the tension transmission means are preferably wound-up on the shaft.

Since the measurement arm is likewise attached radially to the pivot axis, the rotational movement of the rotary knob is thus converted into a pivot movement of the measurement arm in a simple manner, and hence into a movement in the direction of the eye of the measurement body attached to the measurement arm. That is to say, a basically direct mechanical coupling between the rotary knob and the measurement arm is obtained by means of the tension transmission means and, compared to the prior art, it is designed in a particularly simple manner. It is precisely this simplicity which is the greatest advantage of the invention, because by means of this applanation tonometers according to the invention can be produced in a cost-effective manner.

In contrast, no pressure forces have to be transmitted by the tension transmission means. Correspondingly, the tension transmission means can consist of materials which are suitable for transmitting tension forces but unsuitable for transmitting pressure forces.

Furthermore, there is no need for an involved and complex mechanism as required by the prior art which, moreover, has to be balanced and calibrated with much effort and attention to detail. In this manner, the coupling between the rotary knob and the measurement arm is obtained by simple and therefore cost-effective means.

The simple design additionally ensures that all components can be fitted into the housing which at most has the dimensions of corresponding, known tonometer housings, or the equipment can even be housed in a smaller housing than was previously the case. This in turn means that it is possible to design a tonometer according to the invention which externally does not differ from a known tonometer. Consequently, it is possible, for example, to use the same adapters for attaching the tonometer to a slit lamp. Of course, this does not preclude the possibility of nevertheless adapting the external appearance of the tonometer but advantageously retaining the mechanical interfaces for attaching the adapters.

Such applanation tonometers typically have the problem that their zero region is not defined precisely, that is to say the position of the measurement arm in the zero region is not precisely known in ocular pressure measurements. They therefore have to be accurately balanced. This is necessary because, inter alia, such tonometers should be able to determine pressure differences of tenths or even hundredths of a millimeter of a mercury column (mm Hg).

It is for this reason that in a preferred embodiment of the invention, the applanation tonometer comprises at least one balancing weight in the zero region for balancing the measurement arrangement. Although such counterweights are already used in the prior art, their construction there is such that they can and have to be displaced or otherwise adjusted for balancing the measurement arrangement. By contrast, the balancing weights in this embodiment of the invention are fixed and, after installation, can no longer be displaced, adjusted or otherwise changed.

In a particularly preferred embodiment of the invention, this at least one balancing weight is arranged and/or dimensioned in such a manner that changes in spacing between the eye and the applanation tonometer in the zero region are mechanically compensated for so that in the case of changes in spacing of the eye in the zero region, an overall torque acting on the pivot axis is substantially constant, with the overall torque being the sum of individual torques acting on the pivot axis. Specifically, if the spacing between the patient, that is to say the eye to be examined, and the tonometer changes, the centre of gravity of the at least one balancing weight is displaced on the one hand, and, on the other hand, then the rotary force acting on the pivot axis by the tension transmission means also changes. Likewise, the rotary force acting on the pivot axis by the measurement arm with the measurement body also changes.

In the case of such a change in spacing, practically all torques acting on the pivot axis change. The at least one balancing weight is now arranged and/or dimensioned so that a sum of all torques acting on the pivot axis is basically constant.

Or, in other words, even if the spacing between the patient and the tonometer varies in the zero region, the lever pressure on the eye must remain unchanged (or as unchanged as possible) so that this change in spacing does not result in a false intraocular pressure being measured. However, such a change in spacing generates a small rotational movement of the pivot axis, as a result of which the centre of gravity of the measurement optics and the centre of gravity of the at least one balancing weight is changed, and hence there is a torque acting on the pivot axis due to this. Likewise, the torque acting on the pivot axis by the tension transmission means via the first lever arm is of course also changed by this.

The at least one balancing weight is now arranged in terms of weight and position such that, in the case of such a change in spacing between eye and tonometer in the zero region, all changes in torque acting on the pivot axis compensate each other, and thus the torque acting on the pivot axis and hence the force acting on the eye by the measurement body practically remains unchanged in the case of such changes in spacing. As mentioned above, this holds for changes in spacing in the zero region, that is to say within the largest permissible distance of the eye to be measured from the measurement body, or for the measurement interval range of the tonometer.

In principle, this change in torque could also be compensated for electronically in place of such mechanical compensation. However, provision would have to be made for at least one additional sensor in order to be able to determine the precise position of the measurement arm. However, this is connected to increased complexity and would increase the costs of producing the tonometer.

Preferably, provision is made for two such balancing weights. A first balancing weight is used as a counterweight for the measurement arm and is attached to the pivot axis, and a second balancing weight is used as a counterweight for the measurement body and is likewise attached to the pivot axis. Such counterweights can be attached, for example screwed, either directly to the pivot axis, for example on a shaft forming the pivot axis, or indirectly to the pivot axis, for example via a lever, with the desired type of attachment depending on, for example, the spatial conditions within the housing of the applanation tonometer.

In principle, one or more of these counterweights can, of course, be divided into a plurality of appropriately placed and dimensioned individual weights. Likewise, the two individual balancing weights can be combined to form a single, correspondingly heavy and correctly placed balancing weight.

The tension transmission means preferably comprise a spring so that the applanation force does not depend on the speed or force with which the rotary knob is being rotated for example, but that it practically only depends on the angular position of the rotary knob. As a result of this, the applanation force, which can be transmitted to the measurement arm or measurement head by means of the tension transmission means, practically only depends on the deflection of the spring from its normal position, that is to say its unloaded position, and the deflection of the spring in turn depends on the angular position of the rotary knob.

Such a spring can be implemented in a number of different ways. For example, the tension transmission means could be attached to the rotational axis of the rotary knob by means of a spring. However, this presents the problem that the spring constant of this spring would change. To be specific, if the rotary knob is rotated, the tension transmission means attached to the rotational axis of the rotary knob, and hence this spring, are wound-up on the shaft, as a result of which the effective spring length would change. In addition, it could also be the case that the lever arm, by means of which the spring is attached to the rotational axis, changes.

The same problems would exist if the tension transmission means themselves would be in the form of a spring, for example a helical spring.

In principle, spiral or torsion springs could also be used. For example, a spiral spring could be used to attach the tension transmission means to the shaft or to a lever forming the first lever arm. The tension transmission means could also be fixedly attached to the shaft, and the shaft itself could be designed as a torsion spring, or the shaft could be divided into two coaxial, adjacent pieces connected by a torsion spring, with the tension transmission means being attached to one piece and the rotary knob to the other piece. However, these constructions would also have problems because, typically, it is not possible to attain a linear force transmission.

Finally, elastic tension transmission means could also be produced from an appropriate material, such as rubber or a similar material. However, in those cases too, the resultant spring constants are not constant, and hence the generation of the force would not be linear. These two conditions, however, are advantageous for the conversion of the applanation force to the intraocular pressure to be measured to be as simple as possible.

In a preferred embodiment of the invention, the tension transmission means are therefore, by means of a spring, attached to a lever, which is attached to the pivot axis and forms the first lever arm. This makes it possible for the other end of the tension transmission means to be directly attached to the shaft, and thus the tension transmission means can easily and in a problem-free manner be wound-up on the shaft when the rotary knob is rotated about the axis of rotation. Preferably, care has to be taken that the tension transmission means are not wound-up onto the shaft in more than one layer. That is to say, the diameter of the shaft and the length of the tension transmission means to be wound-up onto the shaft should be chosen appropriately, because otherwise the lever arm on the rotational axis would once again change with the rotation.

The spring constant of the spring can be chosen in accordance with the desired properties. Advantageously, helical springs can be considered for this. On the other hand, the lever arm could change in the case of spiral springs because the spring deforms under load. Of course, a helical spring also deforms under load, but this deformation is one-dimensional in the case of such springs, which is why the effective lever arms do not change.

It is very important that the tension transmission means have particular properties so that the applanation force transmitted by the tension transmission means does in fact only depend on the deflection of the spring. On the one hand, the material used in this case must be flexible so that it can be wound-up on the shaft, and, on the other hand, it must have sufficient tensile strength or—in the case of the expected tensile forces—it may only have a very low or no elasticity so that the applanation force can be transmitted without a deformation of the tension transmission means in the longitudinal direction.

Additionally a band, that is to say a long but thin, virtually two-dimensional structure, of such a material has proven to be advantageous, in particular with respect to the regular winding-up onto the shaft of the rotary knob. This is in contrast to, for example, a one-dimensional structure such as a thread or wire, or a three-dimensional structure such as a cuboid or another body. In the case of a thread or a wire with a sufficiently small cross-sectional area which allows a problem-free winding-up onto the shaft, it is possible that the thread or the wire snaps if a high applanation force is set by means of the rotary knob. On the other hand, the danger of a tear is very low in the case of a cuboid or another three-dimensional body; however, it is very probable that the body is not flexible enough to be wound-up on the shaft without problems and without changing the lever arm.

In principle, the tension transmission means can be produced from many different materials. For example, the selection ranges from thin foils and paper to the most diverse plastics. It was found that very thin metal bands, that is to metal bands with a thickness of less than 0.05 mm and a breadth of a few millimeters, are particularly suitable because they allow a very good compromise between flexibility and tensile strength.

It is particularly preferable for a thin band of stainless steel to be used as tension transmission means. This is available on the markets at good conditions. Due to the properties of steel, the thickness of the band should in this case be 0.02 mm or less.

So that the user of such an applanation tonometer can read the intraocular pressure measured with it, the applanation tonometer preferably has a suitable display device by means of which the rotation angle of the rotary knob corresponding to the applanation force can be displayed optically. Instead of, or in addition to, an optical display, the measured pressure could also be output acoustically, for example by a loudspeaker, or, for example, be printed onto paper.

As known from the prior art, the display device can in this case comprise a scale superimposed on the rotary knob, with a reference point positioned on the housing (or vice versa). It could, for example, also be implemented in the manner of the date display in the case of (mechanical) wristwatches, where a disc with a superimposed scale is turned past under a corresponding opening, the date window, or it could be implemented differently using an appropriate mechanism.

However, the display device preferably comprises a display on which the applanation force can be displayed. For example, such a display could be implemented as a 7-segment display, as a liquid crystal display (LCD), or else by means of light emitting diodes or other displays of this type. It is possible that the applanation force set by the rotational angle, using the rotary knob, would still have to be converted into a corresponding electrical signal.

In order to simplify the handling and operation of the equipment, the applanation tonometer is preferably equipped with a microprocessor and an angle transmitter attached to the shaft.

In this case, the angle transmitter is used to convert the set rotation angle corresponding to the applanation force into an electrical signal. This signal can then be converted into a digital value representing the applanation force by the microprocessor. This digital value can then be optically displayed directly by means of the display device.

So that, firstly, the conversion of the rotational angle into a digital value is as simple as possible, and, secondly, the calibration of the angle transmitter is as simple as possible, the latter should preferably be as linear as possible. That is to say, there should be a linear dependence of the electrical signal supplied by the angle transmitter on the angle of rotation. In this case, the characteristic curve of the angle transmitter is specifically formed by a straight line, with two calibration points sufficing to determine the gradient of this straight line which is required to convert the angle of rotation to the applanation force which is in fact applied.

Although it is possible to use a nonlinear angle transmitter, this not only increases the complexity of the conversion itself, but it is also possible that the number of calibration points required for determining the characteristic line of the angle transmitter is substantially increased.

In place of, or in addition to, the optical display of the measured intraocular pressure, it is possible to transmit the latter to an appropriate receiver by means of a radio transmission technique. By way of example, such a receiver can be a different piece of equipment such as a computer, a mobile phone, a PDA (personal digital assistant) or another suitable piece of equipment. The applanation tonometer is equipped with an appropriate transmitter and possibly a corresponding receiver. Indeed, in principle, a transmission technology without wires could be used by means of which signals can be transmitted over large distances. By way of example, a transmission technology could be used which is also used by mobile phones (for example, GSM, UMTS or the like). However, the transmission is typically sent to a piece of equipment which is in the direct vicinity of the applanation tonometer, that is to say within a distance of typically at most a couple of meters, so the applanation tonometer is preferably equipped with a transmitter and possibly a receiver for a short-range radio transmission technique.

Bluetooth is an example of such a short-range radio transmission technology, with corresponding Bluetooth transmitters/receivers being available very cost-effectively as integrated components, that is to say as a chip, and therefore preferably being used.

As already described above, applanation tonometers can be implemented in different ways, with Goldmann applanation tonometers often being used because of their easy manageability, their accuracy and their wide circulation. In such equipment, a circular surface region with a diameter of 3.06 mm is made applanate, that is to say flattened. Since the intraocular pressure (in mmHg) in this case is exactly 10 times higher than the applanation force (measured in gram) required for the applanation, the applanation tonometer according to the invention is preferably in the form of a Goldmann applanation tonometer.

The solution of the object with reference to the method for determining the intraocular pressure of an eye is defined by the features of Claim 11. In this process, the eye is applanate due to a measurement body which is attached to a measurement arm attached radially to a pivot axis, wherein the applanation force required for the applanation is generated by rotating a rotary knob, attached to a shaft, around a rotation axis and is transmitted to the measurement arm by means of a mechanical coupling between the rotary knob and the pivot axis. According to the invention, by means of tension transmission means, the applanation force is transmitted onto the measurement arm by the tension transmission means being attached, on the one hand, to the pivot axis via a first lever arm, and, on the other hand, to the rotational axis of the shaft via a second lever arm.

The method for determining the intraocular pressure using an applanation tonometer according to the invention preferably furthermore comprises the following steps:

The applanation tonometer is typically mounted on a slit lamp in such a way that its user can observe the eye, whose interior pressure is intended to be measured, through both the microscope of the slit lamp and the measurement body of the applanation tonometer. Correspondingly, the measurement body is designed to be at least partly transparent. Next, the patient is positioned in front of the slit lamp, typically with aid of a support such as a chin-rest, for example, such that the eye to be examined can be observed through the microscope and the measurement body. The applanation tonometer is then slightly pre-stressed, so that the measurement arm is virtually in the zero position. The user now moves the slit lamp, and the applanation tonometer fixed in front of it, towards the eye until the measurement body very lightly touches the eye as centrally as possible. Typically, the eye to be examined or both eyes of the patient undergo normal anaesthetization directly before the measurement. In addition, a fluorescein should be applied to the eye for better visualization of the applanation. After this, the position of the applanation tonometer is not changed substantially, but the applanation force is increased by turning the rotary knob until the desired cornea surface is applanate. In the case of a Goldmann applanation tonometer, this is a circular surface region with a diameter of 3.06 mm. Of course, the position of the measurement body on the eye can also still be corrected during a measurement.

Subsequently, the slit lamp with the applanation tonometer can be moved away from the eye, and the intraocular pressure can be read from the applanation tonometer. As mentioned previously, this can be done, for example, by means of a scale superimposed on the rotary knob or the housing, or by means of a display affixed to the housing of the applanation tonometer.

As described above, the intraocular pressure determined in this way in the form of a digital value can also be transmitted to an appropriate receiver by means of a transmitter and radio communication. Such a receiver can for example be integrated into a computer, a mobile phone, a PDA or any other equipment. The transmitted intraocular pressure can for example be stored by the piece of equipment, or it can be displayed on a display device of this piece of equipment. Typically, other details are stored together with the measured intraocular pressure: the name and further personal data, such as the birthday, of the patient, the date of the measurement and whether this is the interior pressure of the left or right eye (left/right recognition). It is possible that some of the data, such as the name and the personal data of the patient, is already known by the receiver, or it can be entered there by the user. Other specifications, such as the left/right specification of the measured eye can be determined by the applanation tonometer itself during the measurement and can be transmitted together with the determined intraocular pressure to the piece of equipment.

The applanation tonometer preferably comprises an appropriate sensor, such as a Hall sensor, for the left/right recognition. This sensor can determine whether the interior pressure of the left or the right eye is being determined by means of a magnet attached to the chin-support of the slit lamp.

The transmission of these specifications from the applanation tonometer to an external piece of equipment can either be carried out automatically after the measurement has been completed, or preferably manually by pressing an appropriate button on the applanation tonometer.

Further advantageous embodiments and combinations of features of the invention emerge from the following detailed description and the totality of the patent claims.

BRIEF DESCRIPTION OF THE DRAWINGS

In the drawings used to explain the exemplary embodiment.

In principle identical parts in the figures are provided with the identical reference symbol.

WAYS OF IMPLEMENTING THE INVENTION

Figure 1:
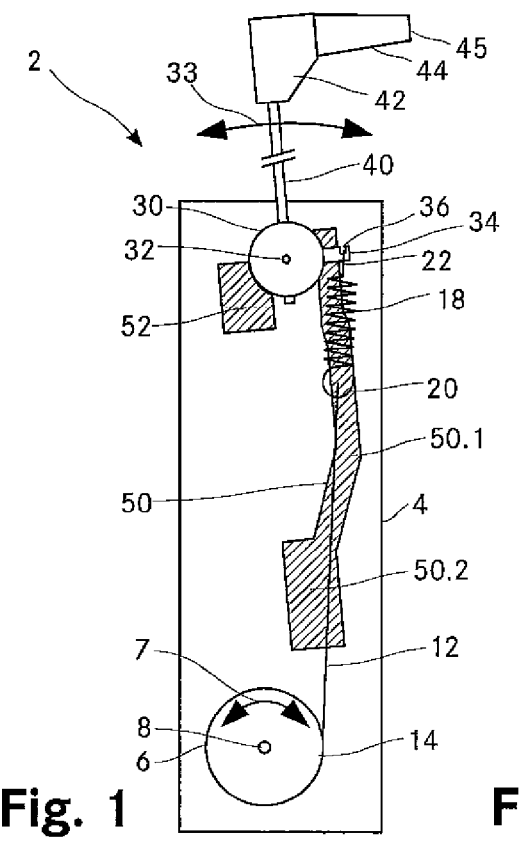
FIG. 1 shows a schematic side view of the interior of an applanation tonometer according to the invention.
Figure 2:
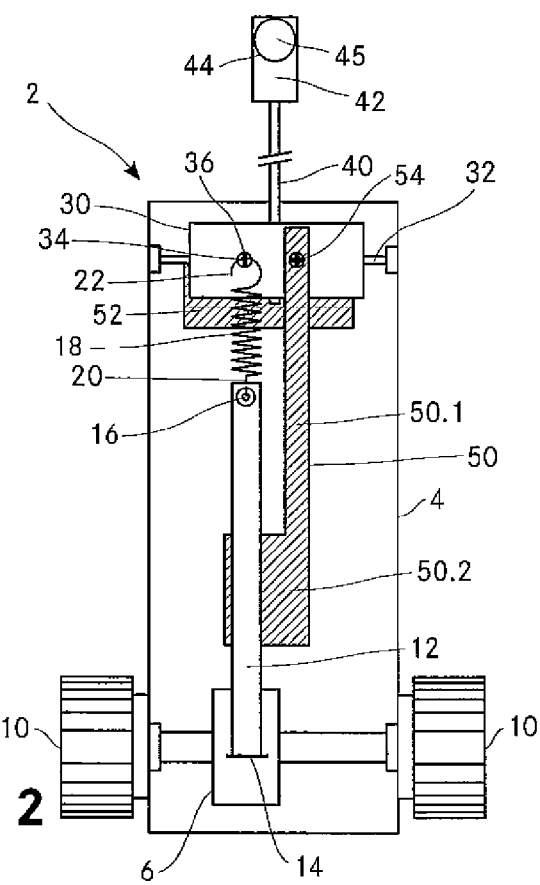
FIG. 2 shows a schematic rear view of the applanation tonometer according to FIG. 1.

FIGS. 1 and 2 show a schematic illustration of an applanation tonometer 2 according to the invention. The interior of the applanation tonometer 2 is shown in a side view in FIG. 1, and in a rear view in FIG. 2. Front and rear sides of the applanation tonometer 2 are defined with respect to the view of the user determining the intraocular pressure of an eye of a patient. That is to say, the rear view is the view of that side of the applanation tonometer 2 facing the patient during the measurement.

The applanation tonometer 2 comprises a housing 4, with a shaft 6 being positioned in the lower region of the housing 4 and the shaft 6 being mounted so that it can be rotated about its rotational axis 8 (indicated by the arrow 7). On at least one side of the housing 4, but preferably on both sides of the housing 4 as indicated, a rotary knob 10 is positioned outside of the housing 4 on the same rotational axis. The lower end of a tension transmission means, in this case a thin steel band 12, is attached to this shaft; by way of example, in this case it is adhesively bonded into an opening 14 in the shaft 6. In this example, the steel band 12 is 0.02 mm thin and has a breadth of a few millimeters. The upper end of the steel band 12 comprises a small opening 16, for example an eye, into which the lower end of a helical spring 18, that is to say the lower end of the wire of the helical spring 18 which is bent to form an eye 20, is hooked into.

A further shaft 30, which is mounted such that it can rotate around its pivot axis 32 (indicated by the arrow 33), is positioned in the upper region of the housing 4, with the pivot axis 32 being aligned parallel to the rotational axis 8. A lever 34 is attached radially to this shaft 30 and it comprises a small recess 36, into which the upper end of the helical spring 18, which likewise has been bent to form an eye 22, is hooked into. The two eyes 20, 22 of the helical spring 18 are in this case aligned perpendicularly to one another, that is to say the planes defined by the eyes 20, 22 are substantially at right angles to one another.

Furthermore, a measurement arm 40, which at its upper end comprises a holder 42 into which the measurement body 44 can be attached, is likewise attached radially to the shaft 30. The measurement body itself corresponds to commercially available measurement bodies and is correspondingly made from a transparent material. For the applanation of the eye, it comprises a circular surface applanation region 45 with a diameter of 3.06 mm in accordance with the Goldmann standard. If a fluorescent dye (for example fluorescein) is put onto the eye directly before the measurement, and the eye is illuminated by a blue light during the measurement, a coloured annulus glows at the edge of that region of the applanation surface 45 where the measurement body displaces the fluorescein. As is usual in the case of Goldmann tonometers, the measurement body furthermore comprises a prism which displaces the upper half of the image against the lower half of the image when looking through the measurement body, with the displacement exactly corresponding to the desired diameter of the surface to be flattened. It follows that from the position of the two visible semicircles, the user can recognize whether the applanation of the surface of the eye is too small, correct or too large and can correspondingly increase the applanation force, leave the applanation force unchanged or decrease the applanation force by rotating the rotary knob.

Two balancing weights 50, 52 are attached to the shaft 30 for balancing the measurement arrangement having the shaft 6, steel band 12, helical spring 18, lever 34, shaft 30 and measurement arm 40 with measurement body 44. In this case, the first balancing weight 50 is used virtually as a counterweight to the measurement arm 40 and comprises a holder 50.1 attached to the shaft 30 by means of a screw 54, and a weight 50.2 attached to the lower end of the holder. It is of course also possible to design the holder 50.1 and the weight 50.2 as one piece. The second balancing weight 52 is used as a counterweight for the measurement body 44 and it is attached directly to the side of the shaft 30 lying opposite to the balancing weight 50 by means of a screw (not shown).

This division of the required counterweights for balancing the measurement arrangement is not mandatory. If the spatial conditions within the housing 4 permit, it is of course possible to only attach a single, correspondingly heavy and correctly positioned counterweight to the shaft 30. For completeness' sake, it should be mentioned that a subdivision into more than two single counterweights would also be possible.

If the helical spring 18 is unloaded, that is to say if the shaft 6 is rotated appropriately far in the counter clockwise direction according to FIG. 1, the measurement arrangement is balanced in such a manner that the measurement arm 40 with measurement body 44 experiences its furthest deflection to the left (that is to say likewise in the counter clockwise direction).

Figure 3:
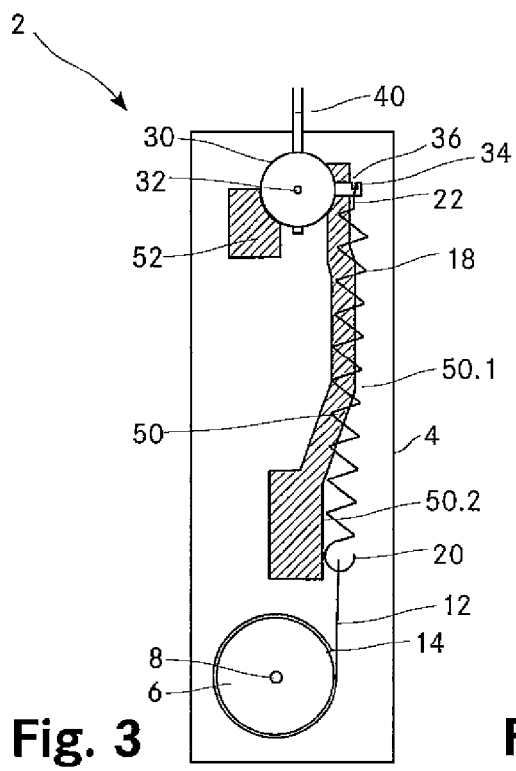
FIG. 3 shows a schematic side view of the applanation tonometer according to FIG. 1 during a measurement with a high applanation force set.
Figure 4:
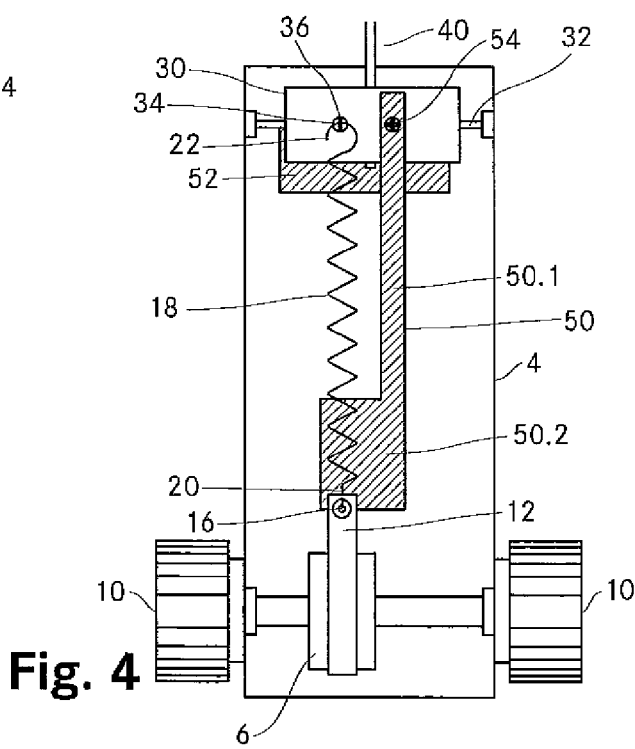
FIG. 4 shows a schematic rear view of the applanation tonometer according to FIG. 3.

This position of the measurement arm 40 is illustrated in FIG. 1. During the measurement, the shaft 6 is now turned in the clockwise direction by means of the rotary knob 10 until the measurement arm 40 is in its zero position, that is to say it is approximately perpendicular, as a result of which the helical spring 18 is slightly pre-tensioned. In this position, the whole applanation tonometer 2 is now moved towards the eye until the measurement head 44 lightly touches the eye to be measured or the cornea of the latter. Thereafter, the applanation pressure acting on the eye is increased by continuing to rotate the shaft 6 in the clockwise direction. As a result of this, the steel band 12 is wound-up onto the shaft 6, and the helical spring 18 is further tensioned. This is illustrated in FIGS. 3 (side view) and 4 (rear view). It should be noted that the length of the steel band 12 wound-up onto the shaft 6 is dimensioned such that the steel band 12 is not wound onto the shaft 6 in multiple layers, as can be seen from FIG. 3. That is to say, this length can be at most $D*\pi$ when the greatest applanation force is being generated (where D is the diameter of the shaft 6 and $\pi$ is the circular constant), because otherwise the effective lever arm and thus the torque acting on the rotational axis 8 changes, which in turn can influence the accuracy of the intraocular pressure measurement.

Since the measurement head 44 is already resting against the eye, the angular position of the measurement arm 40 is only rotated further very slightly when the shaft continues to rotate, whereas the applanation force and the surface of the cornea which is applanate due to the measurement head 44 is increased. If the desired surface is applanate, the applanation force can be calculated from the angular position of the rotary knobs, with it being possible to remove the applanation tonometer 2 from the eye for this purpose.

The applanation force applied is either read from a scale, which is superposed on one or both rotary knobs or on the housing 4, and is calibrated such that—as is usual in the case of Goldmann applanation tonometers—the set applanation force can be read directly from the scale. Alternatively, a digital value corresponding to the applanation force is generated by means of the rotational angle set by the rotary knobs—as in the case of the example illustrated in FIGS. 6 to

8 and described further below—and this digital value is displayed on a display on the housing 4 as the applanation force or the digital value is transmitted to another piece of equipment by means of radio and processed there.

In order to be able to control the transmission of the tension forces between the helical spring 18 and the steel band 12 on the one hand, and the lever 36 on the other hand, as much as possible and in order to design it to be as reproducible as possible, the possibility of the contact point between the spring and the steel band 12 or lever 36 changing again after the calibration of the equipment should be prevented. For this purpose, a bend 37 can optionally be inserted into one or both eyes of the helical spring 18. As a result of this, the force contact point can no longer be changed.

This bend is preferably applied in such a manner that it lies as precisely as possible on the longitudinal axis of the helical spring 18, so that the direction of the force acting on the helical spring 18 corresponds as precisely as possible to the direction of the longitudinal axis of the helical spring. If this bend does not lie on the longitudinal axis, an angle not equal to zero results between the direction of the acting force and the direction of the longitudinal axis, which could possibly lead to falsified measurements.

Figure 6:
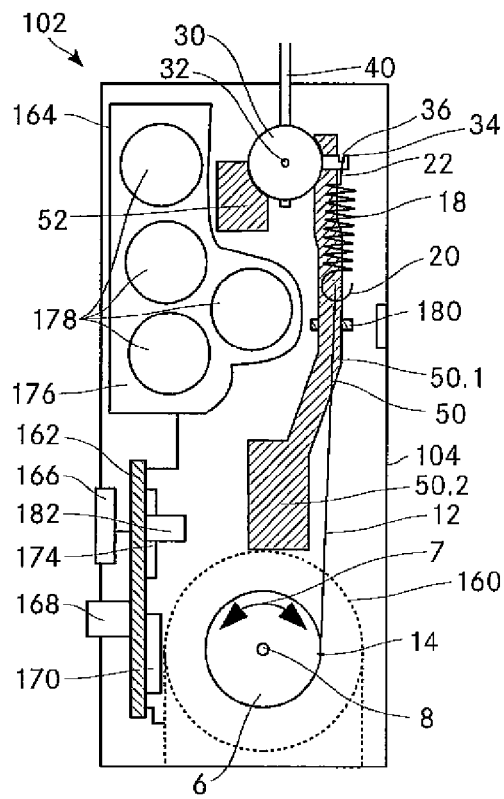
FIG. 6 shows a schematic side view of the interior of a second embodiment of an applanation tonometer according to the invention.
Figure 7:
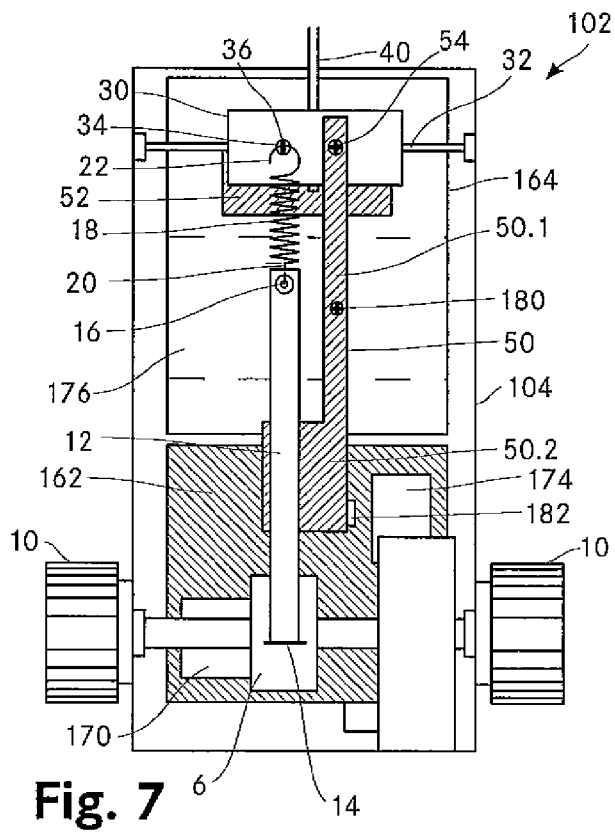
FIG. 7 shows a schematic rear view of the applanation tonometer according to FIG. 6.
Figure 5:
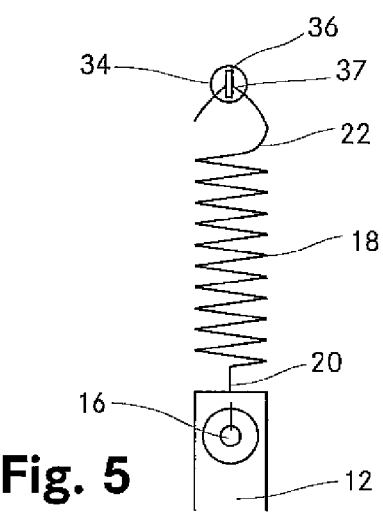
FIG. 5 shows a schematic illustration of the attachment of the tension transmission means to the pivot axis.

FIGS. 6 and 7 illustrate a further exemplary embodiment of an applanation tonometer 102 according to the invention. Mechanically, this piece of equipment is practically identical to the applanation tonometer 2 illustrated in FIGS. 1 to 4. The main difference consists in the fact that the applanation tonometer 102 comprises its own power supply and that the measured applanation pressure corresponding to the intraocular pressure is converted into an electrical signal and can be displayed on a display or transmitted to an external piece of equipment by radio.

For this purpose, the applanation tonometer 102 comprises a few additional components including: an angle transmitter 160, a printed circuit board 162 fitted with various components, a power supply 164, a display 166 and an on-switch 168. The angle transmitter 160 is an electro-mechanical component which is coupled to the shaft 6 and converts the angular position of the shaft 6 into data which can be evaluated electrically, which is possibly encoded and which is typically in the form of an electrical signal. This signal is transmitted to a microprocessor 170 fitted onto the printed circuit board 162, for which purpose the angle transmitter 160 is electrically connected to the printed circuit board 162.

The microprocessor 170 converts the electrical signal emanating from the angle transmitter 160 into a digital value corresponding to the applanation force, and hence the intraocular pressure, and transmits this digital value to the display 166, on which the digital value is displayed. However, the microprocessor must first of all be calibrated appropriately so that for a particular angular position of the shaft 6, it can output the correct intraocular pressure and can display it on the display. The characteristic line of the measurement arrangement, that is to say the relationship between the angular position of the shaft 6 and the applanation force acting on the eye due to the measurement body, must be determined for this purpose.

Since a linear angle transmitter 160 and a helical spring 18 with a linear force generation are used, the characteristic line of the measurement arrangement is linear, and two points on this characteristic line suffice to determine it. Therefore, in order to calibrate the piece of equipment, the rotary knob is turned until the measurement head acts on a test object with a certain pressure, with this pressure being measured by appropriately calibrated pressure measurement equipment. This procedure is repeated for a second pressure value, and the microprocessor is programmed such that, on the display, it outputs the respectively set pressure as the intraocular pressure in the case of these angular positions of the shaft 6. The characteristic line can then be interpolated and extrapolated between these two points, and beyond them, so that the microprocessor can calculate the correct applanation pressure for each angular position of the shaft 6 and output it on the display. As a precaution, it is also possible to determine three or more points of the characteristic line in this manner, so that the characteristic line can, for example, be approximated by a plurality of linear sections. However, in order to minimize the complexity, the number of required calibration points should be reduced as far as possible.

Of course, the applanation tonometer in principle also functions with a nonlinear angle transmitter and a nonlinear helical spring. However, the complexity involved for calibrating the conversion of the angular position of the shaft 6 into the measured intraocular pressure is significantly higher because the characteristic line of the system must be determined by a multiplicity of calibration points. Typically, the effort needed for conversion in the microprocessor is also significantly higher in this case.

Moreover, the applanation tonometer 102 comprises a Bluetooth chip 174 which is likewise fitted onto the printed circuit board 162, and by means of which the intraocular pressure calculated by the microprocessor 170 can be transmitted to an appropriate Bluetooth receiver (not illustrated) by means of Bluetooth technology. For example, this Bluetooth receiver may be integrated into, or connected to, a computer, a mobile phone, a PDA or another piece of equipment suitable for this purpose. The measured and transmitted intraocular pressure can be further processed in any desired manner in the receiving equipment; for example, it can be displayed on a display connected to it, or it can be stored in memory.

The measured intraocular pressure (and, if applicable, further data such as specifications relating to whether it is the left or right eye of the patient) is transmitted when the applanation tonometer 102 is switched on by pressing the on-switch 168. By contrast, neither this nor any other button has to be pressed to switch off the equipment, because the equipment switches itself off in the case of inactivity after a predefined time, typically after a couple of seconds.

The electrical energy required is in this case supplied by the power supply 164. It comprises, for example, a number of batteries 178 housed in a battery housing 176, with it being preferable that commercially available batteries can be used. However, in principle, other sources of energy could, of course, also be used such as solar cells or the applanation tonometer 102 could be attached to an external energy source by means of a cable.

Provision is made for various safety measures to ensure the safety of the patient, that is to say to prevent injury to the eye whose interior pressure is being determined. Firstly, the applanation tonometer 102 comprises mechanical stops which limit the deflection of the measurement arm 40 in both directions. By way of example, for this purpose, an adjustable screw, for example a set screw 180 with a predetermined length, is countersunk into the holder 50.1 of the balancing weight. This abuts, firstly, against the battery housing 176 and, secondly, against the inner side of the housing 104. In this case, the length of the set screw 180 is dimensioned in such way that the measurement head 44 can move backwards and forwards through a distance of approximately 9 mm. From the zero position, it can move approximately 2.5 mm in the direction of the eye and approximately 6.5 mm in the direction away from the eye. The region through which the measurement head 44 can move in the direction of the eye from the zero position—approximately 2.5 mm in the current example—is referred to as the zero region. This zero region corresponds to the maximum permissible distance of the eye from the measurement body 44 and is also referred to as the measurement interval range of the tonometer.

The mechanical stops can of course be implemented differently, for example by appropriately positioned components which correspondingly limit the deflection of the measurement arm 40.

Secondly, the deflection of the measurement arm 40 is monitored. For this purpose, a sensor 182 is fitted to the printed circuit board 162; it determines the distance of the weight 50.2 from the printed circuit board 162 and continuously transmits this to the microprocessor 170. The microprocessor 170 then outputs an alarm, for example in the form of an acoustic signal via a loudspeaker (not illustrated), if this distance is outside of an allowed range. An alarm signal is output in particular if the distance becomes too big. This can prevent the user of the equipment from injuring the eye by inadvertently moving the applanation tonometer 102 closer to the eye, where a measurement arm 40 with a measurement body 44 is already abutting against a stop.

Figure 8:
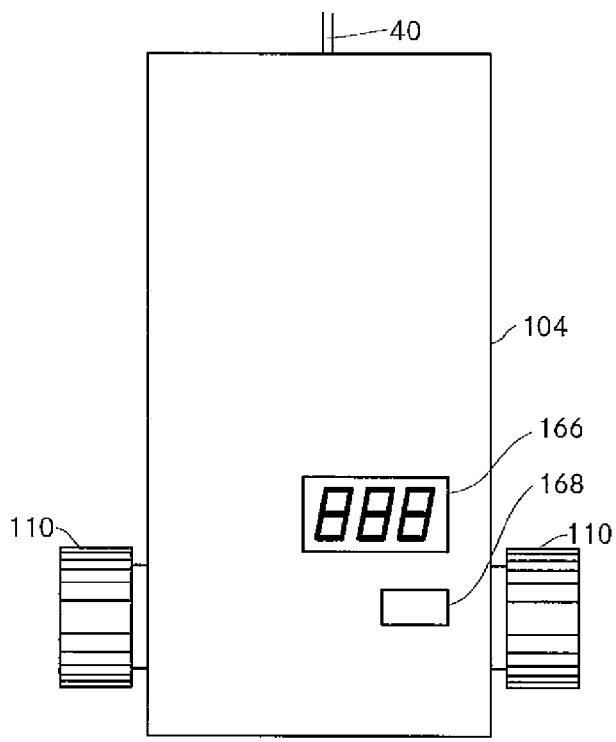
FIG. 8 shows s schematic front view of the applanation tonometer according to FIG. 6.

Finally, FIG. 8 shows a schematic front view of the housing 104 of the applanation tonometer 102 according to FIGS. 6 and 7. The display 166 and the on-switch 168 are illustrated in addition to the housing 104, the rotary knobs 110 and the measurement arm 40.

In summary, it should be noted that an applanation tonometer with a very simple design was developed by the invention which is very cost-effective in its production, but in which no compromises had to be made regarding the quality and the measurement accuracy and measurement reproducibility.

The invention claimed is:

1. A device for determining the intraocular pressure of an eye having a measurement arrangement comprising
a measurement body, attached to a measurement arm, for applanation of the eye and
a rotary knob attached to a shaft and rotatable about a rotational axis of the shaft, with the measurement arm attached radially to a pivot axis, the measurement arrangement further comprising
a mechanical coupling between the rotary knob and the pivot axis, wherein the rotary knob is configured to be rotated around the rotational axis to generate an applanation force required for applanation of the eye,
wherein the mechanical coupling comprises tension transmission means, with the tension transmission means attached to the pivot axis via a first lever arm, and attached to the rotational axis of the shaft via a second lever arm, whereby the tension transmission means is configured to be wound-up by a rotation of the rotary knob about the rotational axis.

2. The device according to claim 1, wherein the measurement arrangement comprises at least one balancing weight in a zero region for balancing the measurement arrangement.

3. The device according to claim 2, wherein the tension transmission means comprises a spring by means of which the tension transmission means are configured to be attached to a lever defining the first lever arm.

4. The device according to claim 2, wherein the at least one balancing weight is arranged and/or dimensioned such that in the case of changes in spacing of the eye in the zero region, an overall torque of the measurement arm and the measurement body acting on the pivot axis is substantially constant, the overall torque being the sum of individual torques acting on the pivot axis as a result of tension transmission by the tension transmission means and as the result of weight shifts of the at least one balancing weight.

5. The device according to claim 4, wherein a first balancing weight is configured to be attached to the pivot axis as a counterweight to the measurement arm, and a second balancing weight is attached to the pivot axis as a counterweight to the measurement body.

6. The device according to claim 4, wherein the tension transmission means comprises a spring by means of which the tension transmission means are configured to be attached to a lever defining the first lever arm.

7. The device according to claim 2, wherein a first balancing weight is configured to be attached to the pivot axis as a counterweight to the measurement arm, and a second balancing weight is attached to the pivot axis as a counterweight to the measurement body.

8. The device according to claim 7, wherein the tension transmission means comprises a spring by means of which the tension transmission means are configured to be attached to a lever defining the first lever arm.

9. The device according to claim 1, wherein the tension transmission means comprises a spring by means of which the tension transmission means are configured to be attached to a lever defining the first lever arm.

10. The device according to claim 9, wherein the spring is a helical spring.

11. The device according to claim 1, wherein the tension transmission means comprises a band consisting of a flexible and inductile material.

12. The device according to claim 11, wherein the tension transmission means comprises a steel band with a thickness of less than 0.05 mm.

13. The device according to claim 12, wherein the steel band has a thickness of less than 0.02 mm.

14. The device according to claim 1, comprising a display device for displaying the rotation angle of the rotary knob corresponding to the applanation force.

15. The device according to claim 1, comprising a microprocessor and an angle transmitter attached to the shaft for converting the set rotation angle corresponding to the applanation force into an electrical signal, convertible into a digital value representing the applanation force by the microprocessor, wherein the digital value is configured to be displayed optically as the applanation force by means of the display device.

16. The device according to claim 15, wherein the device comprises a transmitter for short-range radio-transmission technique by means of which the digital value can be transmitted to an appropriate receiver.

17. The device according to claim 15, wherein the angle transmitter is linear.

18. The device according to claim 1, wherein the device is an applanation tonometer in the form of a Goldmann applanation tonometer.

19. The device according to claim 1, wherein the tension transmission means comprises a band consisting of a flexible and inductile material.

20. The device according to claim 1, wherein the tension transmission means is configured to be wound-up onto the shaft by a rotation of the rotary knob about the rotational axis.

21. A method for determining an intraocular pressure of an eye, in which the eye is applanate due to a measurement body which is attached to a measurement arm attached radially to a pivot axis, comprising the steps of
- generating the applanation force required for the applanation by rotating a rotary knob, attached to a shaft, around a rotation axis
- transmitting the applanation force to the measurement arm by means of a mechanical coupling between the rotary knob and the pivot axis, and
- transmitting by a tension transmission means, the applanation force onto the measurement arm, the tension transmission means being attached to the pivot axis via a first lever arm, and to the rotation axis of the shaft via a second lever arm, with the tension transmission means being wound-up by a rotation of the rotary knob about the rotational axis.

* * * * *